United States Patent
Murayama (10) Patent No.: US 8,740,778 B2
(45) Date of Patent: Jun. 3, 2014

(54) ELECTRONIC ENDOSCOPE SYSTEM

(75) Inventor: Jin Murayama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 168 days.

(21) Appl. No.: 13/360,998

(22) Filed: Jan. 30, 2012

(65) Prior Publication Data

US 2012/0197080 A1 Aug. 2, 2012

(30) Foreign Application Priority Data

Feb. 1, 2011 (JP) .................................. 2011-019565

(51) Int. Cl.
- *A61B 1/045* (2006.01)
- *A61B 1/05* (2006.01)
- *A61B 1/06* (2006.01)
- *A61B 1/04* (2006.01)
- *A61B 1/00* (2006.01)

(52) U.S. Cl.
CPC ............ *A61B 1/043* (2013.01); *A61B 1/00006* (2013.01); *A61B 1/045* (2013.01); *A61B 1/00096* (2013.01); *A61B 1/0638* (2013.01)
USPC .......................................... 600/160; 600/109

(58) Field of Classification Search
CPC .... A61B 1/00096; A61B 1/043; A61B 1/045; A61B 1/051; A61B 1/00186; A61B 1/0638; A61B 1/00004; A61B 1/00006; A61B 1/04
USPC .................. 600/109, 160, 176, 129, 476, 477
See application file for complete search history.

(56) References Cited

U.S. PATENT DOCUMENTS

| | | | |
|---|---|---|---|
| 4,821,117 A * | 4/1989 | Sekiguchi | ........................ 348/68 |
| 5,408,996 A | 4/1995 | Salb | |
| 5,701,903 A | 12/1997 | Sano et al. | |
| 5,749,830 A * | 5/1998 | Kaneko et al. | ................ 600/160 |
| 6,422,994 B1 | 7/2002 | Kaneko et al. | |
| 6,573,513 B2 * | 6/2003 | Hayashi | ..................... 250/458.1 |
| 6,582,363 B2 * | 6/2003 | Adachi et al. | ................. 600/178 |
| 6,638,215 B2 * | 10/2003 | Kobayashi | .................... 600/160 |
| 6,800,057 B2 * | 10/2004 | Tsujita et al. | ................. 600/160 |

(Continued)

FOREIGN PATENT DOCUMENTS

| | | |
|---|---|---|
| JP | 11-295617 A | 10/1999 |
| JP | 2003-19105 A | 1/2003 |

(Continued)

OTHER PUBLICATIONS

Japanese Office Action mailed Feb. 26, 2014 for corresponding Japanese Application No. 2011-019565 and an English translation.

*Primary Examiner* — John P Leubecker (74) *Attorney, Agent, or Firm* — Birch, Stewart, Kolasch & Birch, LLP (57) ABSTRACT

In an electronic endoscope, an insert section has a beam splitter, a CCD, and an EMCCD at its distal end portion. When white light being normal light is applied to an internal body portion, the reflected white light is incident on the CCD through the beam splitter, and a normal image is produced. When the internal body portion is irradiated with special light being excitation light, weak autofluorescence is emitted from specific tissue of the internal body portion. The weak autofluorescence is incident on the EMCCD through the beam splitter. The EMCCD uses an avalanche multiplication effect in its electron multiplier. The EMCCD multiplies signal charge produced from the weak autofluorescence by the electron multiplier, and outputs a high level signal.

13 Claims, 10 Drawing Sheets

(56) References Cited

U.S. PATENT DOCUMENTS

| | | | |
|---|---|---|---|
| 6,982,740 B2* | 1/2006 | Adair et al. | 348/76 |
| 7,393,321 B2* | 7/2008 | Doguchi et al. | 600/109 |
| 7,692,692 B2* | 4/2010 | Ito et al. | 348/222.1 |
| 8,007,433 B2 | 8/2011 | Iketani | |
| 8,208,015 B2* | 6/2012 | Unsai et al. | 348/65 |
| 2001/0009269 A1* | 7/2001 | Hayashi | 250/458.1 |
| 2002/0035330 A1* | 3/2002 | Cline et al. | 600/476 |
| 2007/0002134 A1* | 1/2007 | Ishihara et al. | 348/65 |
| 2009/0036743 A1* | 2/2009 | Yabe et al. | 600/180 |
| 2009/0118578 A1* | 5/2009 | Takasugi et al. | 600/109 |
| 2010/0036262 A1* | 2/2010 | Watanabe et al. | 600/478 |
| 2010/0079587 A1* | 4/2010 | Yoshida | 348/68 |
| 2010/0177180 A1* | 7/2010 | Yamaguchi et al. | 348/65 |
| 2010/0245551 A1* | 9/2010 | Morita | 348/68 |
| 2010/0245619 A1* | 9/2010 | Watanabe et al. | 348/226.1 |
| 2010/0262017 A1* | 10/2010 | Frangioni | 600/476 |
| 2011/0121200 A1* | 5/2011 | Watanabe | 250/458.1 |
| 2011/0295062 A1* | 12/2011 | Gratacos Solsona et al. | 600/109 |
| 2012/0007001 A1* | 1/2012 | Ishihara | 250/459.1 |
| 2012/0127292 A1* | 5/2012 | Yamazaki | 348/68 |
| 2012/0150045 A1* | 6/2012 | Matsumoto et al. | 600/476 |
| 2012/0184812 A1* | 7/2012 | Terakawa | 600/109 |
| 2012/0184813 A1* | 7/2012 | Terakawa | 600/109 |
| 2013/0116508 A1* | 5/2013 | Shida | 600/109 |

FOREIGN PATENT DOCUMENTS

| | | |
|---|---|---|
| JP | 2004-40480 A | 2/2004 |
| JP | 2008-79823 A | 4/2008 |
| JP | 2010-35815 A | 2/2010 |
| JP | 2010-233939 A | 10/2010 |
| WO | WO 02/07587 A2 | 1/2002 |
| WO | WO 03/077749 A2 | 9/2003 |

* cited by examiner

ELECTRONIC ENDOSCOPE SYSTEM

BACKGROUND OF THE INVENTION

1. Field of the Invention

The present invention relates to an electronic endoscope system.

2. Description of the Related Art

Conventionally, electronic endoscope systems are widely used in medical diagnosis and treatment. The electronic endoscope system is constituted of an electronic endoscope having an insert section, a processor device and a light source device connected to the electronic endoscope, and the like.

The electronic endoscope is provided with the insert section to be introduced into a patient's body cavity and an operation section for operating the insert section. In a distal end portion of the insert section, there are formed a lighting window through which illumination light is applied in the patient's body, and an imaging window through which the inside of the body is imaged. In the electronic endoscope, an image sensor captures through the imaging window an image of an internal body portion to be examined under the illumination light applied through the lighting window. The processor device applies various types of processing to an image signal outputted from the image sensor, and produces an observation image used for the diagnosis. The observation image is displayed on a monitor connected to the processor device. The light source device has an adjustable-intensity white light source to supply the electronic endoscope with the illumination light. The illumination light is led to the distal end portion through a light guide routed through the electronic endoscope, and is applied from the lighting window to the internal body portion through a lighting optical system.

The insert section is required to have a small diameter, with the aim of reducing a physical burden on the patient. For this reason, the distal end portion contains the single image sensor in general, but there is known an electronic endoscope system that contains plural image sensors in the distal end portion to improve clarity of the image (refer to Japanese Patent Laid-Open Publication Nos. 2004-40480 and 2008-79823). For example, the Japanese Patent Laid-Open Publication No. 2004-40480 discloses a technique in which a half mirror splits an optical path in two directions, and two image sensors disposed in the two paths capture images with different exposure times. A composite image of the two images facilitates expanding a dynamic range. The Japanese Patent Laid-Open Publication No. 2008-79823 discloses a technique in which a dichroic prism splits incident light into green light (G light), red light (R light), and blue light (B light). An image of the G light is merged with an image of the R and B light to improve resolution.

In recent years, there is known a method in which the internal body portion is imaged with application of specific wavelength light (hereinafter called special light), to emphasize specific tissue such as a tumor and a capillary vessel in a superficial mucous membrane. For example, in narrow band imaging, blue light in a narrow wavelength band is applied to the internal body portion, and its reflected light is captured. In autofluorescence imaging, autofluorescence that is emitted from specific tissue inside the human body in response to application of excitation light is captured. In agent fluorescence imaging, a fluorescent labeling agent is administered to the patient in advance, and agent fluorescence that is emitted from the labeling agent in response to application of excitation light is captured. In infrared imaging, infrared light is applied to the internal body portion, and its reflected light is captured.

Among the light to be captured as described above, the autofluorescence, the agent fluorescence, or the infrared light produces a weak signal. To image such weak light, a specific image sensor is provided in U.S. Pat. No. 8,007,433 corresponding to Japanese Patent Laid-Open Publication No. 2007-50106. In the U.S. Pat. No. 8,007,433, a prism splits light incident from the internal body portion in two with respect to the wavelength of 500 nm. Then, two types of images, that is, an image of light with wavelengths of 500 nm or less and an image of light with wavelengths of more than 500 nm are captured separately, to obtain a high-quality special light image.

In capturing the weak fluorescence emitted from the internal body portion, even if the special light such as the excitation light emitted from the light source is filtered out and only the fluorescence is captured, a clear image suitable for the diagnosis is not necessarily obtained because the fluorescence itself is too weak. Thus, in the Japanese Patent Laid-Open Publication No. 2008-79823, for example, a signal obtained from one of two image sensors is amplified to produce an autofluorescence image. The amplification of the signal by image processing, however, has a disadvantage that a noise component is also amplified proportionally. Therefore, when the weak light such as the autofluorescence and the agent fluorescence is captured, it is desired that a signal of the light to be captured itself is amplified to obtain a clear image, in addition to cutting out the special light.

SUMMARY OF THE INVENTION

An object of the present invention is to improve the quality of a special image that captures weak light reflected or emitted from an internal body portion in response to application of special light.

To achieve the above and other objects, an electronic endoscope system according to the present invention includes an insert section to be introduced into a human body, a normal light emitting section for emitting white light to an internal body portion, a special light emitting section for emitting special light to the internal body portion, a first imaging section, a second imaging section, a light splitting section, and a monitor. The first imaging section is provided in a distal end portion of the insert section, and captures a first image of the internal body portion irradiated with the white light. The second imaging section is provided in the distal end portion of the insert section, and captures a second image of the internal body portion irradiated with the special light. The second imaging section has an electron multiplying section for multiplying signal charge that is photoelectrically converted from weak light incident from the internal body portion. The light splitting section splits light incident from the internal body portion, and heads the light for the first imaging section and the second imaging section. The monitor displays the first and second images of the internal body portion.

The weak light may be fluorescence, and the special light may be excitation light for producing the fluorescence. The second imaging section may include an excitation light cut filter for cutting out the excitation light reflected from the internal body portion.

The monitor may display the first image captured by the first imaging section and the second image captured by the second imaging section in a tiled manner.

The electronic endoscope system may further include an image composition section for producing a composite image by superimposing the second image captured by the second imaging section on the first image captured by the first imaging section. The composite image is preferably displayed on the monitor.

The first imaging section and the second imaging section are preferably disposed so as to have an equal field of view to each other with respect to the light splitting section.

The electronic endoscope system may further include a cooling section for cooling the second imaging section. The cooling section may include a Peltier device or a heat sink.

The light splitting section may include a beam splitter or a half mirror.

The first imaging section may include a CCD image sensor, and the second imaging section may include an EMCCD image sensor. The EMCCD (electron multiplying CCD) image sensor multiplies the weak image signal with use of avalanche multiplication effect in its charge transfer section, and outputs the multiplied image signal.

A start of readout of the signal charge from the second imaging section is preferably performed in synchronization with a start of readout of any frame of the first imaging section.

The fluorescence may be autofluorescence emitted by itself from specific tissue inside the human body in response to irradiation with the excitation light. The excitation light may be violet light having a wavelength of 400 nm to 420 nm. In another case, the fluorescence is emitted from a fluorescent labeling agent administered to the internal body portion when being stimulated by the excitation light. The second imaging section may capture an infrared fluorescence image, and the infrared fluorescence image may be displayed on the monitor together with the first image captured by the first imaging section for comparison.

When time required by the first imaging section to accumulate signal charge or read out the signal charge is defined as one frame period, the second imaging section may accumulate the signal charge for two frame periods, and read out the accumulated signal charge in a next single frame period. In another case, the first imaging section may alternately perform accumulation and readout of the signal charge at a cycle of the one frame period, and the second imaging section may alternately perform accumulation and readout of the signal charge at a cycle of the one frame period. In this case, while one of the first and second imaging sections performs the accumulation of the signal charge, the other preferably performs the readout of the signal charge.

According to the present invention, it is possible to obtain the clear special image.

BRIEF DESCRIPTION OF THE DRAWINGS

For more complete understanding of the present invention, and the advantage thereof, reference is now made to the following descriptions taken in conjunction with the accompanying drawings, in which.

DETAILED DESCRIPTION OF THE PREFERRED EMBODIMENTS

Figure 1:
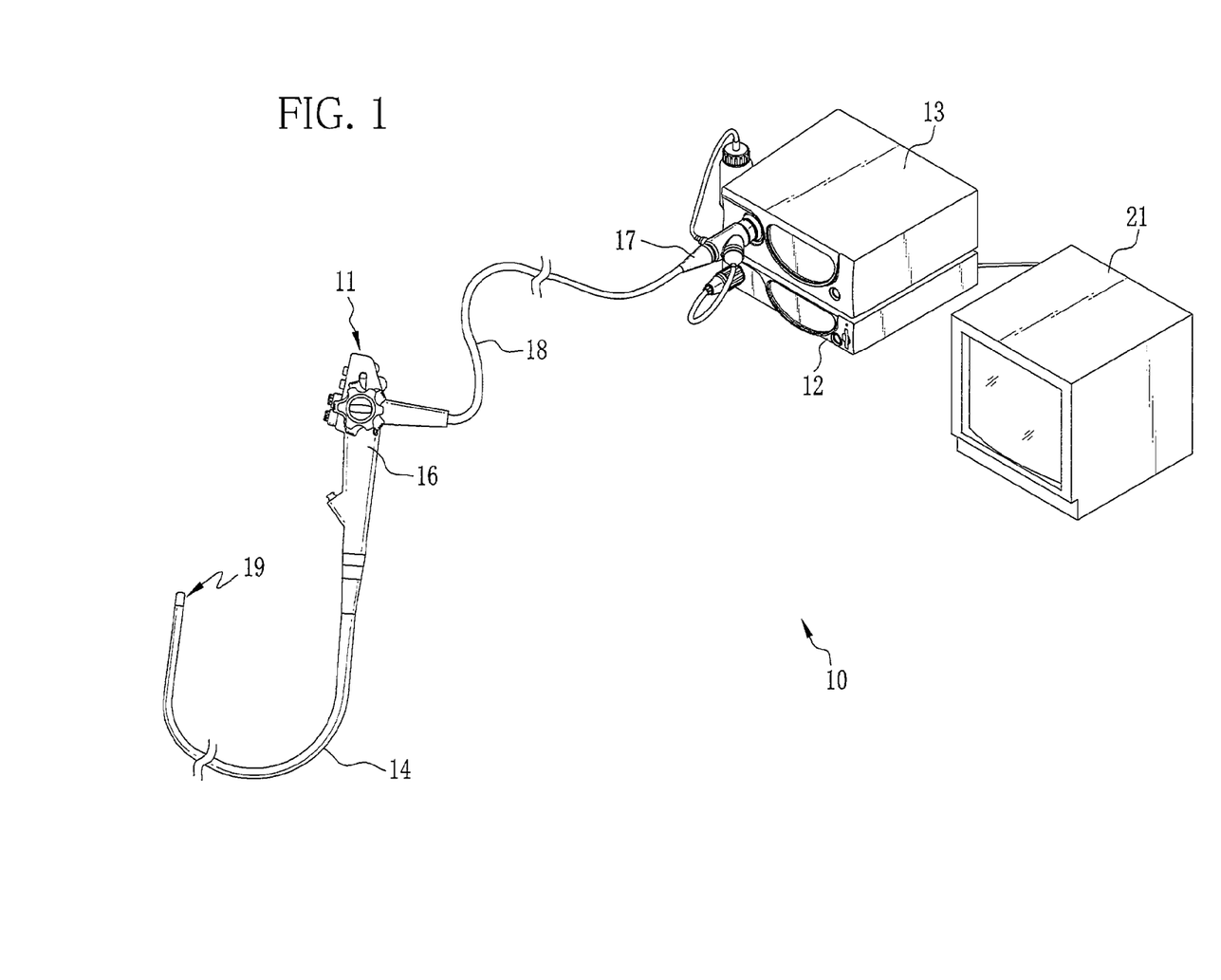
FIG. 1 is a schematic view of an electronic endoscope system.

As shown in FIG. 1, an electronic endoscope system 10 is constituted of an electronic endoscope 11, a processor device 12, and a light source device 13. The electronic endoscope 11 includes a flexible insert section 14 to be introduced into a patient's body cavity, an operation section 16 coupled to a base end of the insert section 14, a connector 17 connected to the processor device 12 and the light source device 13, and a universal cord 18 for connecting the operation section 16 to the connector 17. The insert section 14 contains at its distal end portion 19 two types of image sensors, that is, a CCD 43 (see FIG. 2) for capturing an image under white light and an EMCCD (electron multiplying CCD) 46 (see FIG. 2) for capturing an image under special light.

On the operation section 16, there are provided operation members including an angle knob for flexibly bending the distal end portion 19 in a desired direction, an airing/watering button for ejecting air or water from the distal end portion 19, a release button for capturing and storing a static observation image, and a zoom button for zooming in or out on the observation image displayed on a monitor 21. The operation section 16 is provided with a medical instrument insertion port on its distal end side, into which a medical instrument such as an electrocautery is inserted. The medical instrument insertion port is coupled to a medical instrument outlet provided in the distal end portion 19 through a channel provided in the insert section 14.

The processor device 12 is electrically connected to the electronic endoscope 11 and the light source device 13. The processor device 12 performs centralized control of the electronic endoscope system 10. The processor device 12 supplies electric power to the electronic endoscope 11 through the universal cord 18 and a cable provided in the insert section 14, and controls operation of the CCD 43 and EMCCD 46. Also, the processor device 12 receives image signals outputted from the CCD 43 and EMCCD 46 through cables, and produces various types of image data. The image data produced by the processor device 12 is displayed as the observation image on the monitor 21 connected to the processor device 12 with a cable.

Figure 2:
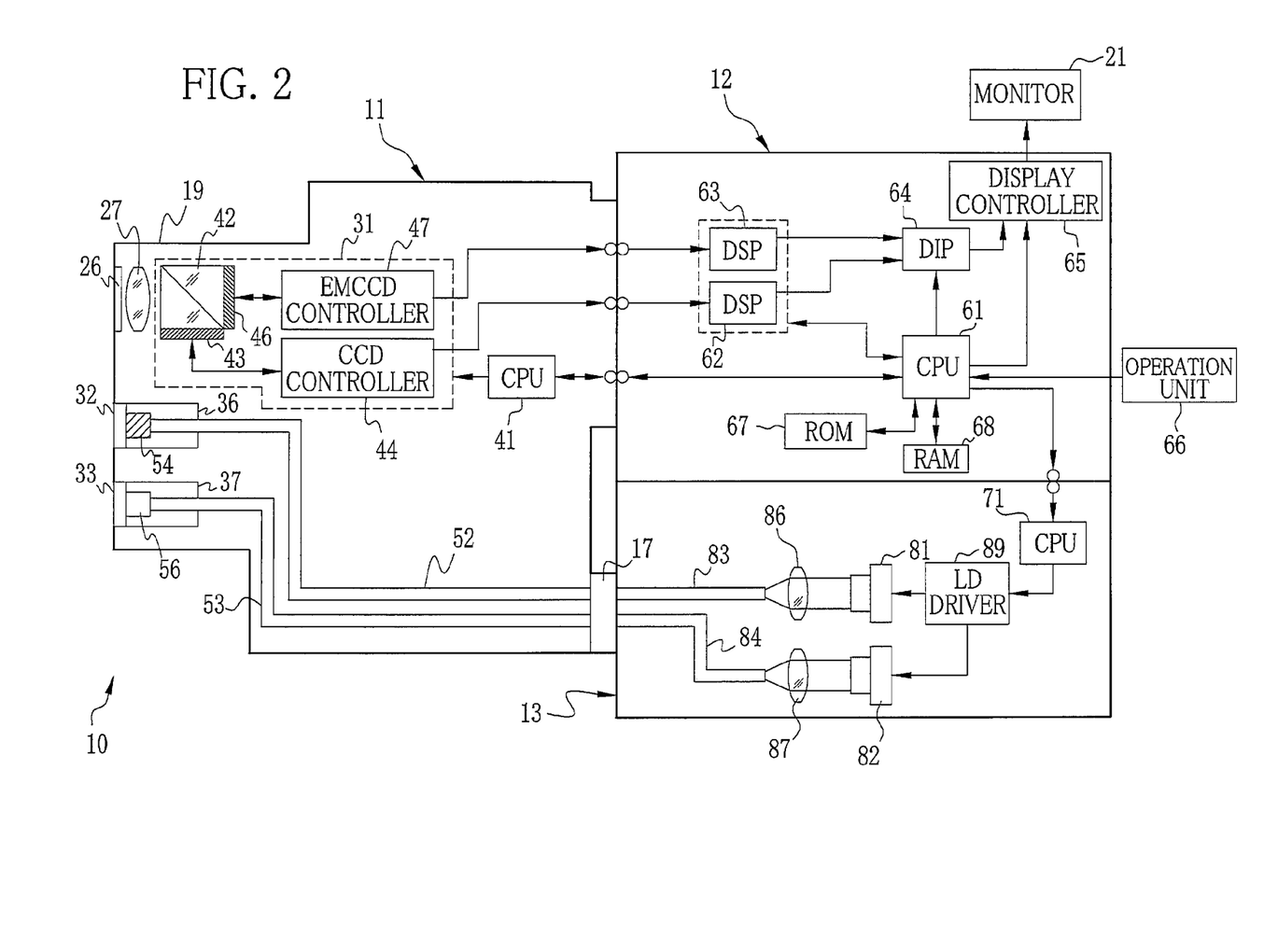
FIG. 2 is a block diagram showing the electrical structure of the electronic endoscope system.

As shown in FIG. 2, the electronic endoscope 11 is provided with an objective optical system 27 and a camera head assembly (CHA) 31 in the recess of an imaging window 26, and light projecting units 36 and 37 in the recesses of lighting windows 32 and 33, respectively.

The imaging window 26 made of a transparent material is provided in an end surface of the distal end portion 19. Light from an internal body portion is incident on the imaging window 26, and is led through the objective optical system 27 to the CHA 31. The objective optical system 27 including a lens forms an image of the internal body portion on imaging planes of the CCD 43 and the EMCCD 46 through a beam splitter 42 provided in the CHA 31.

The CHA 31 is an assembly for imaging the internal body portion under control of a CPU 41. The CHA 31 includes the beam splitter 42, the CCD 43, the EMCCD 46, a CCD controller 44, an EMCCD controller 47, and the like. The beam splitter 42, the CCD 43, and the EMCCD 46 are contained in the distal end portion 19. The CPU 41, the CCD controller 44, and the EMCCD controller 47 are contained in the operation section 16, the connector 17 of the universal cord 18, or the like.

Figure 3:
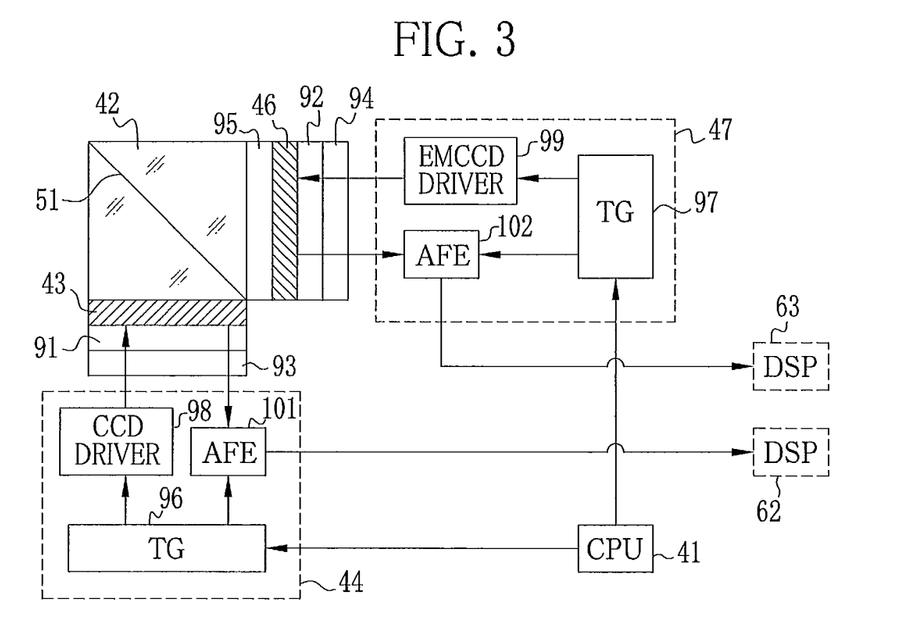
FIG. 3 is a schematic view of a camera head assembly.

The beam splitter 42 splits the light incident from the objective optical system 27 in two directions heading for the CCD 43 and the EMCCD 46. As shown in FIG. 3, the beam splitter 42 takes the shape of a cube, which is composed of two prisms in the shape of triangle poles disposed adjoining oblique surfaces. A semitransparent layer 51 is provided in the interface between the prisms. The semitransparent layer 51 transmits a part of the incident light, and reflects the remains. The split by the semitransparent layer 51 does not depend on the wavelength of the incident light, but the semitransparent layer 51 transmits and reflects the light of every wavelength at substantially the same ratio. For example, the semitransparent layer 51 transmits 30% to 70% of the incident light, and reflects the remaining 70% to 30%. Note that, the transmittance and reflectivity of the semitransparent layer 51 may be other values, and are arbitrary determined in accordance with the sensitivity of the CCD 43 and the EMCCD 46, and the like. Using the semitransparent layer 51, the beam splitter 42 makes 30% to 70% of the light incident from the internal body portion enter into the EMCCD 46, and 70% to 30% of the incident light enter into the CCD 43. A special light cut filter 95 is disposed between the beam splitter 42 and the EMCCD 46 to cut the special light, that is, excitation light. The special light cut filter 95 prevents the EMCCD 46 from receiving the reflected excitation light. The special light cut filter 95 preferably has a transmittance of the excitation light of 0.1% or less. The special light cut filter 95 may be integrated into a light exit surface of the beam splitter 42 on an EMCCD side.

The CCD 43 is an image sensor that takes an image of the internal body portion under the white light (hereinafter called normal light). The CCD 43 is disposed such that its imaging plane faces to a light exit surface of the beam splitter 42. The operation of the CCD 43 is controlled by the CCD controller 44. The CPU 41 controls the operation timing of the CCD 43 through the CCD controller 44. The CCD controller 44 obtains the image signal outputted from the CCD 43, and subjects the image signal to an A/D conversion. Then, the CCD controller 44 outputs the image signal to a DSP 62 of the processor device 12. In taking a moving image, the frame rate of the CCD 43 is set at 30 pfs or 60 pfs in general, but may be set at an arbitrary rate from 1 to 200 fps. The electronic endoscope system 10 can record the static image, in addition to the moving image.

The EMCCD 46 is an image sensor that images weak autofluorescence emitted from living tissue of the internal body portion. In the EMCCD 46, the autofluorescence is converted into signal charge by photoelectric conversion. The EMCCD 46 multiplies the signal charge, and outputs the multiplied signal charge as an image signal, though details will be described later. The operation of the EMCCD 46 is controlled by the EMCCD controller 47. The CPU 41 controls the operation timing of the EMCCD 46 through the EMCCD controller 47. The EMCCD controller 47 obtains the image signal outputted from the EMCCD 46, and subjects the image signal to an A/D conversion. Then, the EMCCD controller 47 outputs the image signal to a DSP 63 of the processor device 12.

The lighting windows 32 and 33 made of a transparent material are provided in the end surface of the distal end portion 19 to illuminate the inside of the human body. The normal light is applied through the lighting window 32. The excitation light (hereinafter called special light), which causes the living tissue to emit the autofluorescence, is applied through the lighting window 33. The lighting windows 32 and 33 are integrated with the light projecting unit 36 and 37, respectively, as described later. FIG. 2 shows one set of the lighting window 32 and the light projecting unit 36 for the normal light, and one set of lighting window 33 and the light projecting unit 37 for the special light, for simplicity's sake. In actual fact, however, plural sets of the lighting window and the light projecting unit are provided such that a field of view (imaging area) of the electronic endoscope 11 is uniformly irradiated with the normal light and the excitation light.

The light projecting units 36 and 37 project light, which is led from the light source device 13 through optical fibers 52 and 53, to the internal body portion through the lighting windows 32 and 33, respectively. A tip end of the light projecting units 36 and 37 is sealed with protective glass. The protective glass is exposed from the end surface of the distal end portion 19, and functions as the lighting windows 32 and 33.

To the light projecting unit 36 for projecting the normal light to the internal body portion, blue laser light is led from the light source device 13 through the optical fiber 52. The light projecting unit 36 has a plate of a phosphor 54 at its tip end. The phosphor 54 composed of YAG or BAM ($BaMgAl_{10}O_{17}$), for example, absorbs a part of the blue laser light ejected from the optical fiber 52, and pumps green to yellow light. The remaining blue light that transmits through the phosphor 54 with dispersion is combined with the pumped green to yellow light emitted from the phosphor 54, so the light projecting unit 36 projects the normal light being artificial white light.

The light projecting unit 37 projects the special light to the internal body portion. The special light is led from the light source device 13 through the optical fiber 53 to the light projecting unit 37. The light projecting unit 37 has a light diffusing member 56 at its tip end. The light diffusing member 56 diffuses the special light ejected from the optical fiber 53. Thus, the special light projected from the light projecting unit 37 to the internal body portion has certain expansion of irradiation, and covers the entire imaging area of the electronic endoscope 11.

The processor device 12 is provided with a CPU 61, the digital signal processors (DSPs) 62 and 63, a digital image processor (DIP) 64, a display controller 65, an operation unit 66, a ROM 67, a RAM 68, and the like.

The CPU 61 is connected to each part through a data bus, an address bus, and control lines (none of them is shown), and performs centralized control of the entire processor device 12. The ROM 67 stores various types of data including various programs (an OS, application programs, and the like) used for the control of the processor device 12, graphic data, and the like. The CPU 61 reads out the required programs or data from the ROM 67, and loads the programs or data to the RAM 68 being a working memory, and processes the read programs in succession. Also, the CPU 61 retrieves text data including an examination date, the patient's name, a doctor's information, and the like from the operation unit 66 or through a network such as LAN, and writes the text data to the RAM 68.

Furthermore, the CPU 61 inputs a control signal to the CPU 41 of the electronic endoscope 11. Based on the control signal, the CCD 43 and the EMCCD 46 accumulate the signal charge for a certain period at start/end timing adjusted in accordance with an imaging mode, which determines the type of light to be applied to the internal body portion, light application timing, and the like. The CPU 41 of the electronic endoscope 11 controls the operation of the CCD 43 and EMCCD 46 by actuating a CCD driver 98 and an EMCCD driver 99 in accordance with the control signal inputted from the CPU 61. When normal imaging by the CCD 43 and special imaging by the EMCCD 46 are performed alternately, the CPU 41 inputs a timing adjustment signal for commanding this operation to the CCD controller 44 and the EMCCD controller 47. The normal imaging and the special imaging may be performed alternately with different charge accumulation periods between the CCD 43 and the EMCCD 46. Furthermore, the normal imaging and the special imaging may be performed not alternately at a frequency of 1:1, but a frequency of 2:1, 4:1, 8:1, or 16:1 such that the special imaging is performed less number of times. In response to the update of each of the normal and special images, the displayed static image may be updated. It is not necessary to update both the normal and special images at a time.

The CPU 61 inputs the same control signal as that to be inputted to the CPU 41 of the electronic endoscope 11 to a CPU 71 of the light source device 13. Thus, the light source device 13 applies the normal light and the special light to the internal body portion in accordance with the imaging mode in synchronization with the imaging timing of the CCD 43 and the EMCCD 46.

The DSP 62 applies various types of signal processing such as color separation, color interpolation, gain correction, white balance adjustment, and gamma correction to the image signal inputted from the CCD 43, and produces an image (hereinafter called normal image) under the normal light. The normal image produced by the DSP 62 is written to a working memory of the DIP 64. The DSP 62 also produces first ALC data that includes an average luminance value being an average of luminance of every pixel in the produced normal image, for example, and inputs the first ALC data to the CPU 61. The first ALC data is used for automatic control of the amount of the illumination light. The CPU 61 transfers the first ALC data inputted from the DSP 62 to the CPU 71 of the light source device 13.

The DSP 63 applies various types of signal processing such as gain correction and gamma correction to the image signal inputted from the EMCCD 46, and produces an image (hereinafter called special image) of the autofluorescence emitted from the internal body portion in response to the application of the special light. The special image produced by the DSP 63 is written to the working memory of the DIP 64. The DSP 63 also produces second ALC data based on contrast and sharpness of the special image, and inputs the second ALC data to the CPU 61. The CPU 61 transfers the second ALC data to the CPU 71 of the light source device 13.

The DIP 64 applies various types of image processing such as electron multiplication, color enhancement process, and edge enhancement process to the normal image produced by the DSP 62 and the special image produced by the DSP 63. The DIP 64 also produces a composite image by superposition of the normal image and the special image, in accordance with the setting of display on the monitor 21. The normal and special images after being subjected to the image processing by the DIP 64 and the composite image produced by the DIP 64 are temporarily written to a VRAM (not shown) as the observation images, and then are inputted to the display controller 65.

The display controller 65 obtains the observation image from the VRAM, and displays the observation image on the monitor 21. The display controller 65 receives from the CPU 61 the graphic data stored on the ROM 67 and the RAM 68. The graphic data includes a mask for covering the observation image except for the region of interest, the text data such as the examination date, the patient's name, and the doctor's information, the GUI, and the like. The display controller 65 applies image overlaying process, by which the graphic data is overlaid on the observation image obtained from the VRAM. Then, the display controller 65 converts the processed image into a video signal (component signal, composite signal, and the like) that is compatible with a display format of the monitor 21, and outputs the video signal to the monitor 21. Thus, the observation image is properly displayed on the monitor 21.

The operation unit 66 is an input device including an operation panel, a mouse, and a keyboard provided in the processor device 12. The CPU 61 operates each part of the electronic endoscope system 10 in response to operation signals inputted from the operation unit 66 and the operation section 16 of the electronic endoscope 11.

In addition to the above, the processor device 12 includes a compression circuit for compressing various images in a predetermined format (for example, JPEG format), a medium I/F for writing the compressed image to a removable medium in response to the operation of the release button, a network I/F for controlling transmission of various types of data through the network such as the LAN, and the like. These circuits are connected to the CPU 61 through the data buses and the like.

The light source device 13 has an LD 81 for normal light emission and an LD 82 for special light emission. The LD 81 for normal light emission emits the blue laser light having a center wavelength of 445 nm. The blue laser light is led into an optical fiber 83 through a lens 86 and the like. The optical fiber 83 is connected to the optical fiber 52 of the electronic endoscope 11 via the connector 17. Thus, the blue laser light emitted from the LD 81 is led into the light projecting unit 36. Transmitting through the phosphor 54, the blue laser light is made into the normal light to be applied to the internal body portion.

The light emission amount of the LD 81 is variable, and is controlled by the CPU 71 through an LD driver 89. The CPU 71 automatically adjusts the light emission amount of the LD 81 based on the first and second ALC data inputted from the CPU 61 of the processor device 12, to adjust the amount of the normal light applied to the internal body portion. For example, in capturing the normal image by itself, the CPU 71 automatically controls the light emission amount of the LD 81 based on the first ALC data optimally for the normal imaging. In capturing the normal image and the special image at the same time, the CPU 71 automatically controls the amount of the normal light with taking the second ALC data into consideration in addition to the first ALC data, such that the reflected normal light incident on the EMCCD 46 does not degrade the sharpness and contrast of the special image.

The LD 82 for special light emission emits violet laser light having a center wavelength of 405 nm. The violet laser light is led into an optical fiber 84 through a lens 87 and the like. The optical fiber 84 is connected to the optical fiber 53 of the electronic endoscope 11 via the connector 17. Thus, the violet laser light emitted from the LD 82 is applied to the internal body portion from the light projecting unit 37. In response to the application of the special light, the weak autofluorescence of a small amount is emitted from the internal body portion. Accordingly, in capturing the special image, the light emission amount of the LD 82 is always set at its maximum level, so as to maximize the amount of the autofluorescence.

The CPU 71 controls turn-on/off timings of each individual LD 81 or 82 through the LD driver 89 based on the control signal from processor device 12.

As shown in FIG. 3, the CHA 31 includes the beam splitter 42, the CCD 43, the EMCCD 46, Peltier devices 91 and 92, heat sinks 93 and 94, and the special light cut filter 95.

As described above, the CCD 43 is so disposed that its imaging plane faces to the beam splitter 42. On a rear surface of the CCD 43, the Peltier device 91 and the heat sink 93 are provided. When being driven by direct current, the Peltier device 91 absorbs heat in a surface contacting the CCD 43, and releases the heat from a surface contacting the heat sink 93. The heat sink 93 efficiently releases the heat occurring from the CCD 43 and cools the CCD 43. In a like manner, the EMCCD 46 is so disposed that its imaging plane faces to the beam splitter 42. In a rear surface of the EMCCD 46, the Peltier device 92 and the heat sink 94 are provided. The heat sink 94 efficiently releases heat occurring from the EMCCD 46 and cools the EMCCD 46.

The special light cut filter 95 is disposed between the beam splitter 42 and the EMCCD 46. Out of the light incident from the beam splitter 42, the special light cut filter 95 cuts off the special light and allows only the autofluorescence to enter into the EMCCD 46. Thus, the EMCCD 46 captures only the autofluorescence that is emitted from the internal body portion in response to the application of the special light. Note that, the amount of the autofluorescence is much smaller than that of the special light. The autofluorescence has a peak wavelength at about 500 nm and a broad wavelength band extending from 450 nm to 700 nm in general, though it depends on the type of living tissue from which the autofluorescence is emitted. Thus, the special light cut filter 95 is formed so as to attenuate the blue special light having the center wavelength of 405 nm to 0.1% or less, and transmit green to red light at approximately 100%, for example.

The CCD controller 44 includes a timing generator (TG) 96, the CCD driver 98, and an analog frontend circuit (AFE) 101. The TG 96 inputs a clock signal to the CCD driver 98 based on the control signal inputted from the CPU 41. The CCD driver 98 converts the clock signal inputted from the TG 96 into control pulses, and inputs the control pulses to the CCD 43 to control the operation of the CCD 43. The AFE 101 samples the image signal outputted from the CCD 43 with removal of noise, and amplifies the image signal. The AFE 101 digitizes the image signal, and inputs the digital image signal to the DSP 62. The AFE 101 is operated based on the clock signal inputted from the TG 96 under control of the CPU 41. The CPU 41 adjusts an amplification factor of the image signal based on the control signal inputted from the CPU 61 of the processor device 12, for example.

The EMCCD controller 47, as with the CCD controller 44, includes a TG 97, the EMCCD driver 99, and an AFE 102. The operation of the components of the EMCCD controller 47 is the same as those of the CCD controller 44 described above, except that the EMCCD controller 47 controls the operation of the EMCCD 46.

Figure 4:
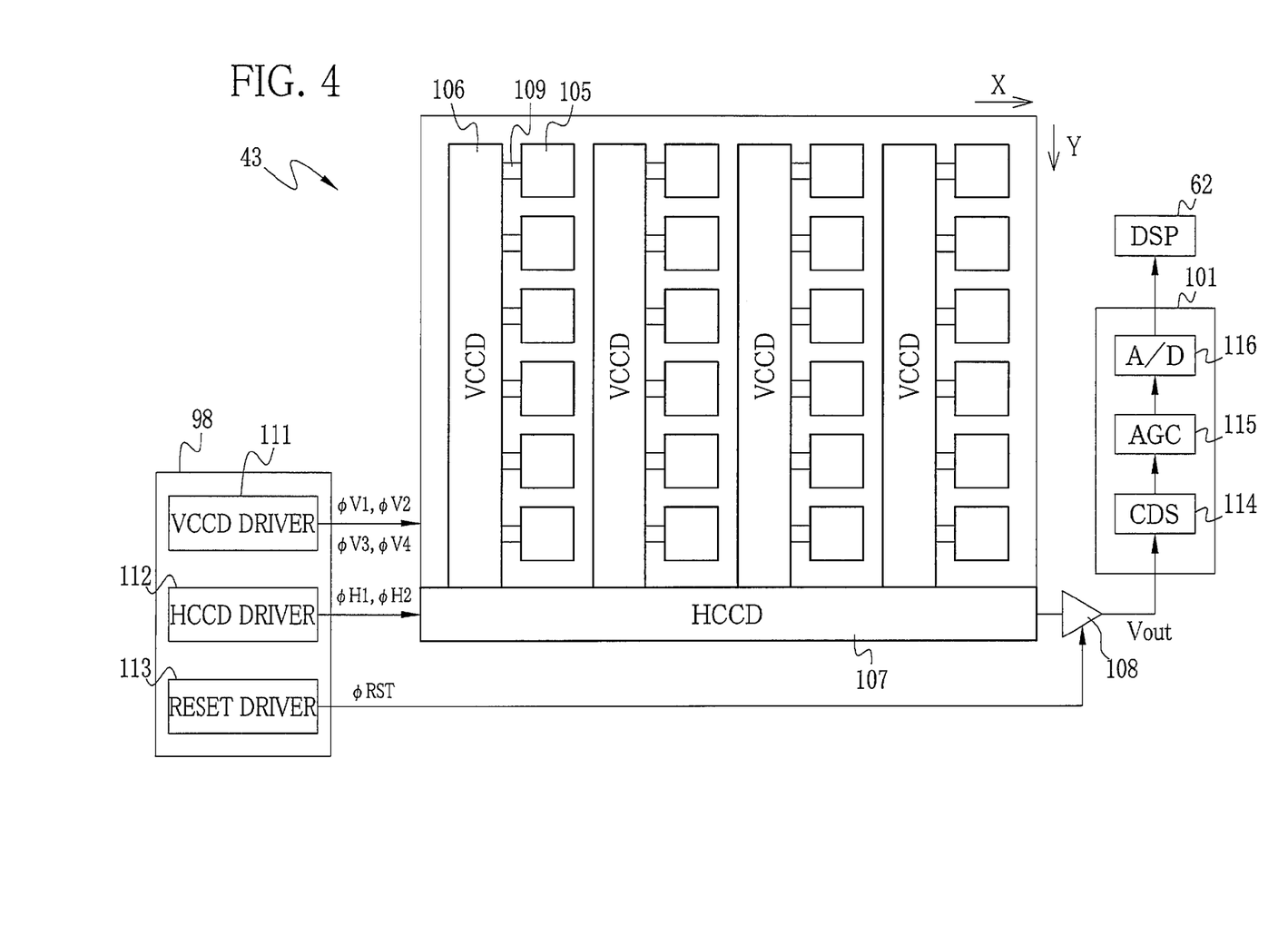
FIG. 4 is a schematic view of a CCD.

As shown in FIG. 4, the CCD 43 has photodiodes (PDs) 105, VCCD regions 106, a HCCD region 107, and an output section 108.

The PDs 105 are arranged into a matrix. Each PD 105 converts the incident light into the signal charge by photoelectric conversion, and accumulates the signal charge. The imaging plane refers to an area in which the PDs 105 are arranged. The CCD 43 is provided with a color filter having plural color segments, which are formed into the same pattern as that of the PDs 105. The color filter is, for example, a RGB primary color filter, a CMY complementary color filter, or a CMYG complementary color filter having a Bayer array.

One VCCD 106 is provided for each column of the PDs 105 arranged in a vertical direction (Y direction). Every PD 105 is connected to the VCCD 106 through a readout gate 109. The signal charge is read out from each PD 105 through the readout gate 109 to the VCCD 106. The VCCD 106 transfers the signal charge read out from the PDs 105 in the vertical direction, and inputs the signal charge to the HCCD 107.

The VCCD 106, having plural vertical transfer electrodes, is driven in four phases by vertical transfer pulses φV1 to φV4 inputted from a VCCD driver 111 of the CCD driver 98. Out of these vertical transfer electrodes, the vertical transfer electrodes to which the first and third vertical transfer pulses φV1 and φV3 are applied also function as gate electrodes of the readout gates 109.

The HCCD 107 transfers the signal charge of one row, which is successively transferred from every VCCD 106, in a horizontal direction (X direction). The HCCD 107, having plural horizontal transfer electrodes, is driven in two phases by horizontal transfer pulses φH1 and φH2.

To an output end of the HCCD 107, a floating diffusion amplifier is provided as the output section 108. The output section 108 converts the signal charge transferred by the HCCD 107 into a voltage signal on a pixel (PD 105) basis, and output the image signal Vout.

The CCD driver 98 includes the VCCD driver 111, a HCCD driver 112, and a reset driver 113.

The VCCD driver 111 generates the vertical transfer pulses φV1 to φV4 by converting the level of the clock signal for vertical transfer. The VCCD driver 111 inputs the vertical transfer pulses φV1 to φV4 to the vertical transfer electrodes used for control of the VCCDs 106, in order to control the charge accumulation period of each pixel and the transfer of the signal charge in the vertical direction.

The HCCD driver 112 generates the horizontal transfer pulses φH1 and φH2 by converting the level of the clock signal for horizontal transfer. The HCCD driver 112 inputs the horizontal transfer pulses φH1 and φH2 to horizontal transfer electrodes used for control of the HCCD 107, in order to control the transfer of the signal charge in the horizontal direction.

The reset driver 113 generates a reset pulse φRST by converting the level of the clock signal for charge reset. The reset driver 113 inputs the reset pulse φRST to the output section 108, in order to abandon the signal charge of each pixel after being converted into the voltage and outputted as the image signal Vout.

The AFE 101 includes a correlated double sampling circuit (CDS) 114, an automatic gain controller (AGC) 115, and an A/D converter (A/D) 116. The CDS 114 applies the correlated double sampling processing to the image signal outputted from the CCD 43, to remove noise occurring due to the drive of the CCD 43. The AGC 115 amplifies the image signal following the removal of the noise by the CDS 114. The A/D 116 converts the image signal amplified by the AGC 115 into the digital image signal of a predetermined bit number.

Figure 5:
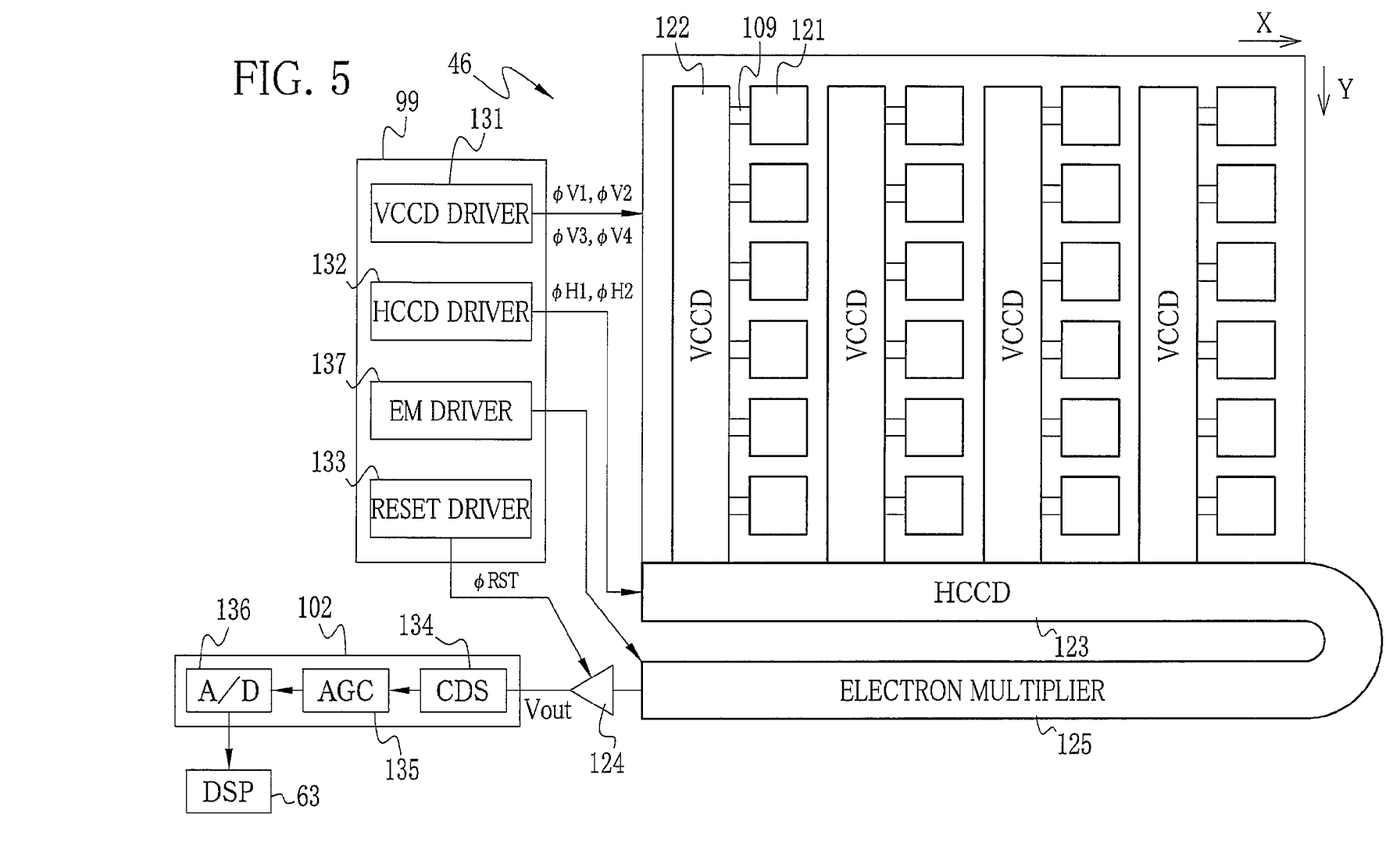
FIG. 5 is a schematic view of an EMCCD.

As shown in FIG. 5, the EMCCD 46 includes PDs 121, VCCDs 122, a HCCD 123, an output section 124, and the like, as with the CCD 43. The operation of the EMCCD 46 is the same as that of the CCD 43. Ditto with a VCCD driver 131, a HCCD driver 132, a reset driver 133, a CDS 134, an AGC 135, and an A/D 136. However, the EMCCD 46 is provided with an electron multiplier 125 between the HCCD 123 and the output section 124. Note that, the EMCCD 46 refers to an electron multiplying CCD that multiplies the weak image signal with taking advantage of an avalanche multiplication effect in its charge transfer section, and outputs the multiplied image signal.

The electron multiplier 125 composes the charge transfer section driven by a higher voltage than that of the HCCD 123, and is driven by an EM pulse inputted from an EM driver 137. The EM driver 137 is contained in the EMCCD driver 99, and generates the EM pulse from the clock signal inputted from the TG 97. While the signal charge from the HCCD 123 is transferred through the electron multiplier 125, the signal charge is accelerated by a high electric field corresponding to the drive voltage. The accelerated signal charge collides against a crystal lattice, and generates new charge (a negative-electrode and positive-hole pair). This new charge generated by an impact ionization effect is also accelerated by the high electric field, and further generates other new signal charge by the avalanche multiplication effect. Thereby, the electron multiplier 125 multiplies the signal charge transferred from the HCCD 123. The signal charge multiplied by the electron multiplier 125 is inputted to the output section 124.

The EMCCD 46 multiplies the signal charge using the electron multiplier 125, as described above. The electron multiplier 125 can multiply only the signal charge with suppressing noise, as distinct from the case of multiplying the image signal, and results in improving an S/N ratio. Therefore, the EMCCD 46 can produce the clear image of the weak autofluorescence.

In the electronic endoscope system 10 having the above structure, the beam splitter 42 splits the optical path, and the CCD 43 and the EMCCD 46 always form the images of the internal body portion at the same time. Thus, it is possible to obtain the normal image and the special image substantially at the same time.

Figure 6:
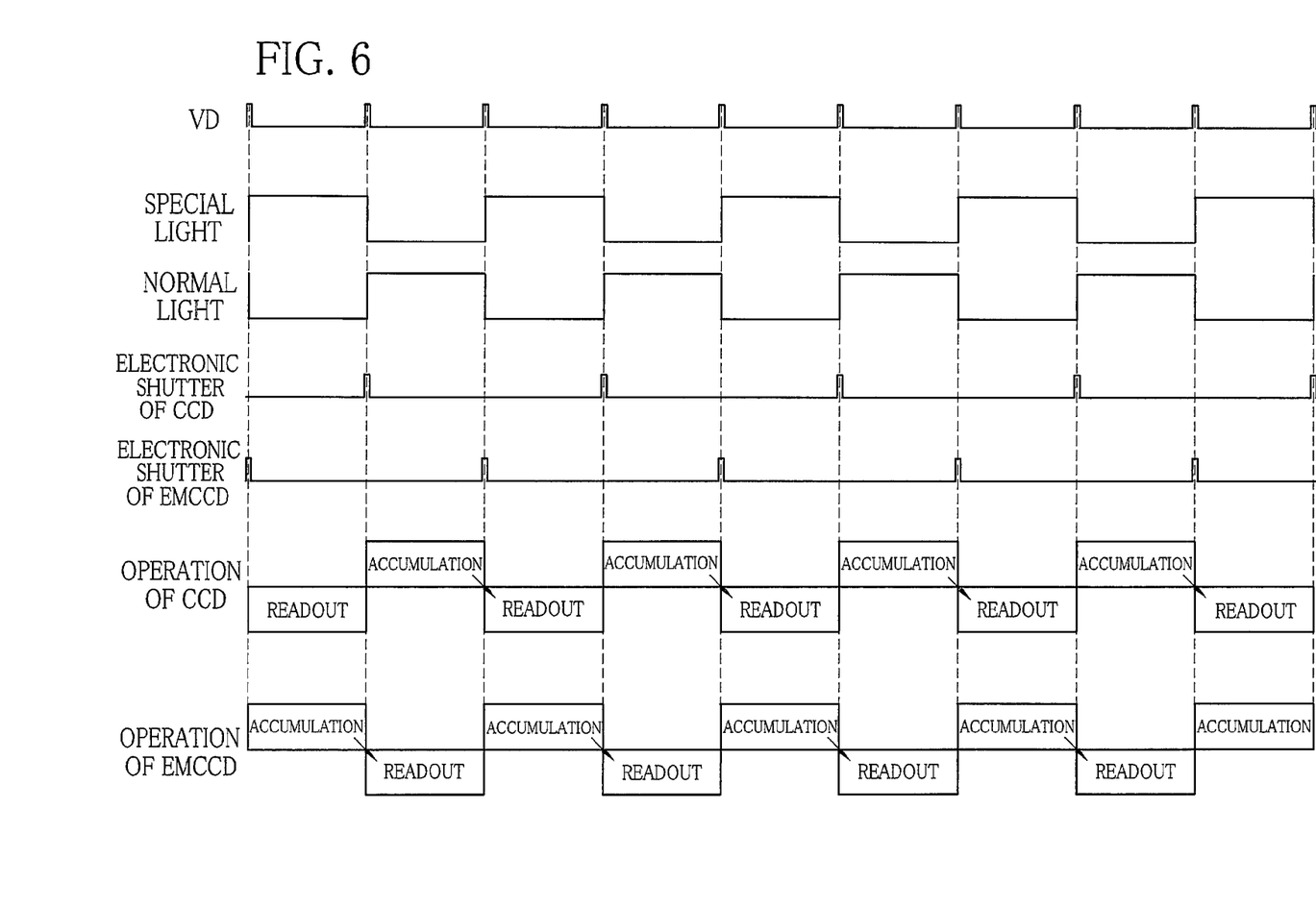
FIG. 6 is a timing chart showing the operation of the CCD and EMCCD according to one embodiment of the present invention.

FIG. 6 shows an example of the operation of the CCD 43 and EMCCD 46 in the case of capturing the normal image and the special image substantially at the same time. A single frame period represents an interval at which a vertical synchronization signal VD is inputted from the CPU 41 to the TGs 96 and 97 as the control signal. Upon the input of the vertical synchronization signal VD, the TG 96 inputs the clock signal corresponding to the vertical synchronization signal VD to the VCCD driver 111. The VCCD driver 111 generates the vertical transfer pulses from the vertical synchronization signal and inputs the vertical transfer pulses to the PDs 105 of the CCD 43, so the signal charge accumulated in the PDs 105 is read out to the VCCDs 106. Similarly, the TG 97 inputs the clock signal to the VCCD driver 131, and the VCCD driver 131 generates and inputs the vertical transfer pulses to the PDs 121 of the EMCCD 46, so the signal charge accumulated in the PDs 121 is read out to the VCCDs 122.

The CCD 43 accumulates the signal charge for the single frame period, and outputs the accumulated signal charge in the next frame period as the image signal. To be more specific, a charge accumulation period (exposure period) begins at the input of an electronic shutter pulse to the CCD 43 and ends at the input of the next vertical synchronization signal VD. A readout period in which the signal charge accumulated in the CCD 43 is read out begins upon the completion of the charge accumulation period and continues until the input of the next vertical synchronization signal VD. Accordingly, the CCD 43 captures the single normal image in every two frame periods. Note that, the normal light is applied to the internal body portion in synchronization with the charge accumulation period of the CCD 43, and is not applied during the readout period of the CCD 43 and a charge accumulation period of the EMCCD 46. The input timing of the electronic shutter pulse is variable in a period until the input of the next vertical synchronization signal VD, and can be determined in accordance with the amount of the incident light.

The special light is applied to the internal body portion in synchronization with the charge accumulation period of the EMCCD 46, and is not applied in the other periods. As with the CCD 43, the EMCCD 46 accumulates the signal charge for the single frame period, and outputs the accumulated signal charge in the next frame period as the image signal. Accordingly, the EMCCD 46 captures the single special image in every two frame periods. The operation of the EMCCD 46 is the same as that of the CCD 43. The charge accumulation period of the EMCCD 46 begins at the input of an electronic shutter pulse to the EMCCD 46 and ends at the input of the next vertical synchronization signal VD. A readout period of the EMCCD 46 begins upon the completion of the charge accumulation period of the EMCCD 46 and continues until the input of the next vertical synchronization signal VD. However, the CCD 43 operates out of phase with the EMCCD 46 by one frame period, so the normal imaging by the CCD 43 and the special imaging by the EMCCD 46 are carried out alternately at a cycle of one frame period. Note that, the input timing of the electronic shutter pulse is variable in a period until the input of the next vertical synchronization signal VD, and can be determined in accordance with the amount of the incident light.

By alternately capturing the normal image and the special image at the cycle of one frame period, as described above, it is possible to observe the normal image and the special image substantially at the same time. This eliminates the need for switching an imaging mode, and simplifies the operation of the doctor. Also, comparison between the normal image and the special image that are captured at substantially the same time can improve the accuracy of diagnosis.

Figure 7:
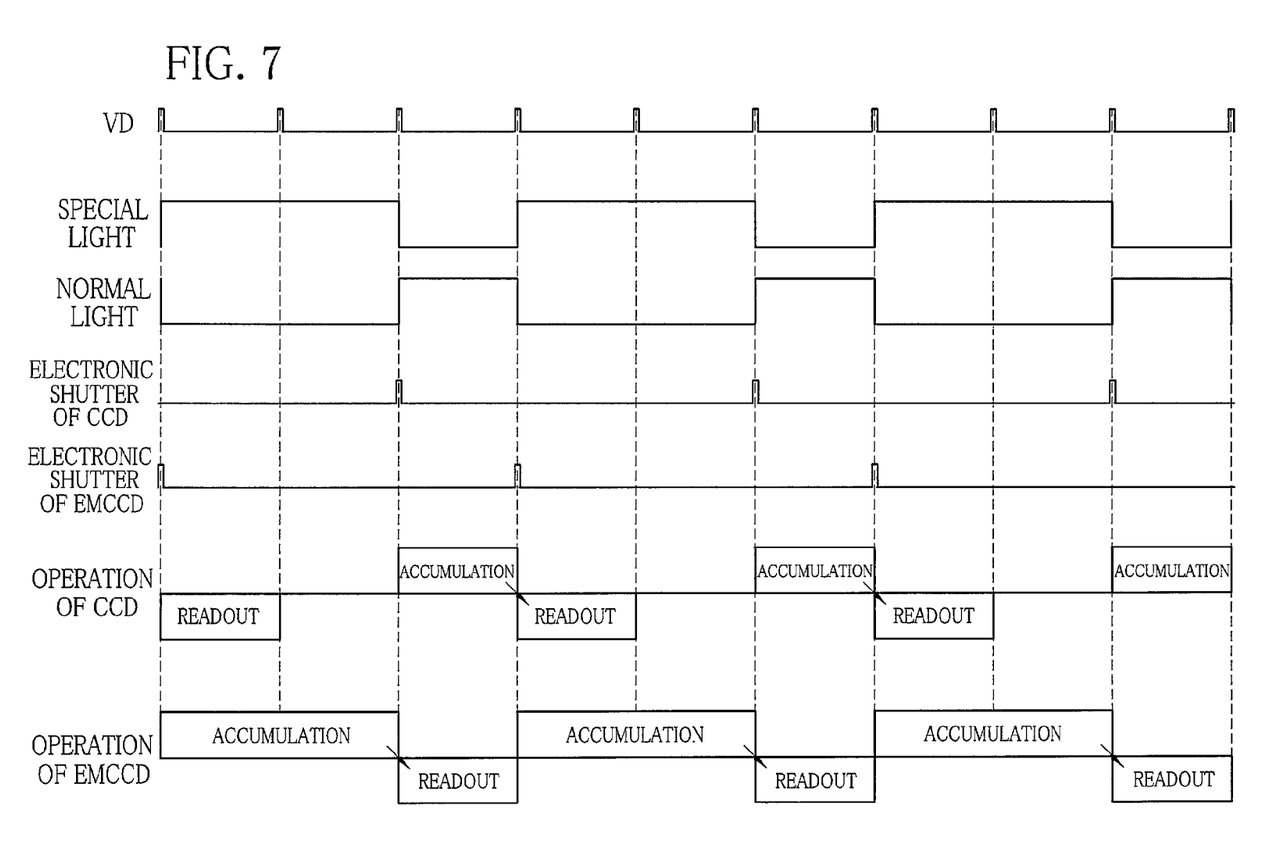
FIG. 7 is a timing chart showing the operation of the CCD and EMCCD according to another embodiment.
Figure 8:
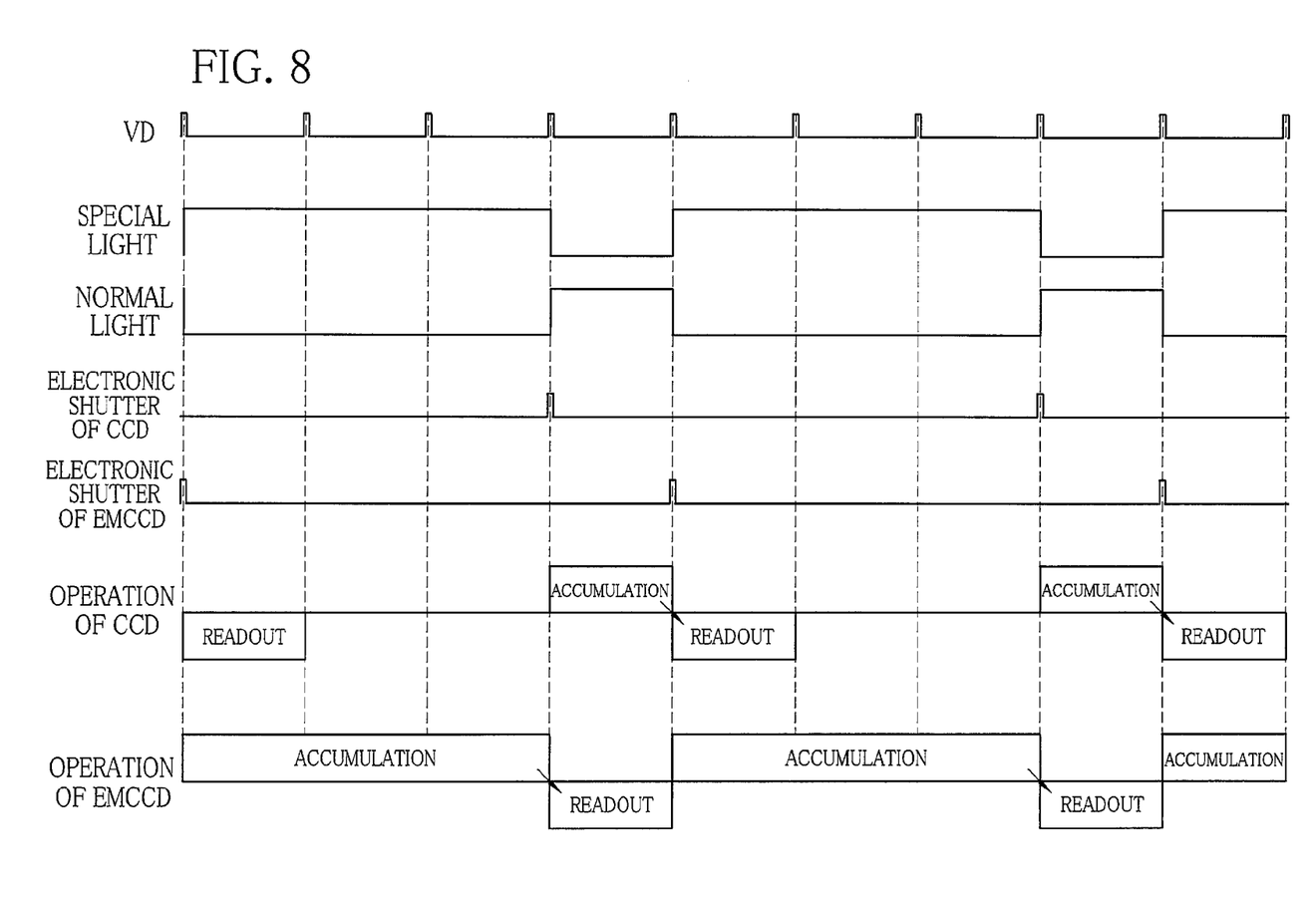
FIG. 8 is a timing chart showing the operation of the CCD and EMCCD according to further another embodiment.

In the above embodiment, the normal imaging by the CCD 43 and the special imaging by the EMCCD 46 are alternately carried out at the cycle of one frame period, which is defined as the input interval of the vertical synchronization signal. However, since the autofluorescence is weak, the charge accumulation period of the EMCCD 46 is preferably elongated. For example, as shown in FIG. 7, the EMCCD 46 may accumulate the signal charge for the two frame periods. In this case, the time required to read out the signal charge is still the one frame period, and the CCD 43 accumulates the signal charge in synchronization with the readout period of the EMCCD 46 to capture the normal image. Also, the charge accumulation period of the EMCCD 46 may be further elongated to an integral multiple of the one frame period, for example, to the three frame periods as shown in FIG. 8.

Figure 9:
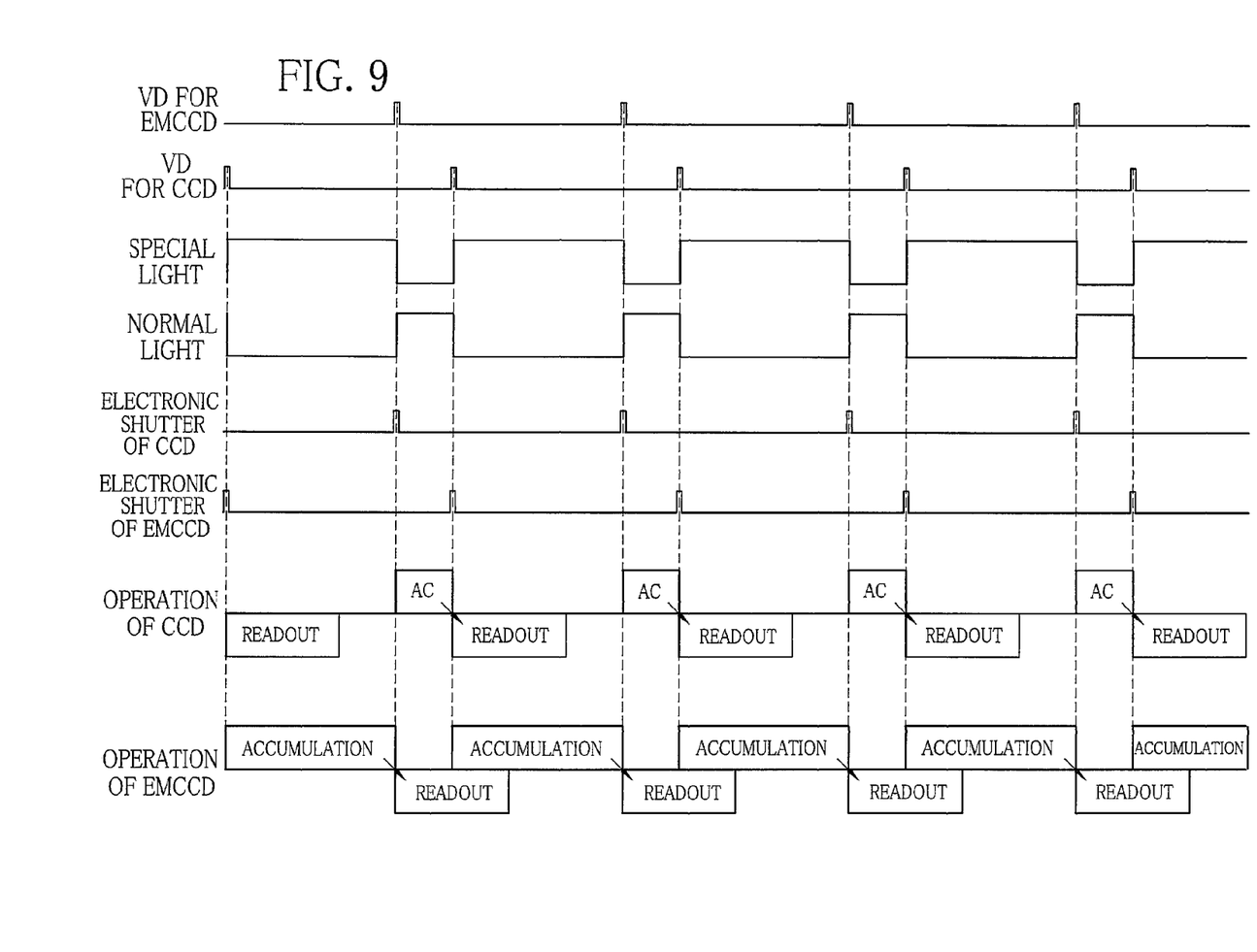
FIG. 9 is a timing chart showing the operation of the CCD and EMCCD according to further another embodiment.

In the above embodiment, the vertical synchronization signal VD is inputted to the CCD 43 and the EMCCD 46 at the same timing, and the normal image and the special image are alternately captured at the cycle of the one or more frame periods, which are defined as the interval of rising edges of the vertical synchronization signal VD. However, as shown in FIG. 9, different vertical synchronization signals may be inputted to the CCD 43 and the EMCCD 46, for example. The input of the electronic shutter pulse of the CCD 43 is synchronized with the vertical synchronization signal VD of the EMCCD 46, while the input of the electronic shutter pulse of the EMCCD 46 is synchronized with the vertical synchronization signal VD of the CCD 43. Then, the charge accumulation period of the CCD 43 is set shorter than the one frame period, while the charge accumulation period of the EMCCD 46 is set longer than the one frame period. Note that, the time required to read out the signal charge from the CCD 43 or the EMCCD 46 is the one frame period. By shortening the charge accumulation period of the CCD 43 and elongating the charge accumulation period of the EMCCD 46, the interval between the charge accumulation periods of the EMCCD 46 is reduced. Therefore, it is possible to improve efficiency in the special imaging, in other words, increase a frame rate of the special imaging by the EMCCD 46.

Figure 10:
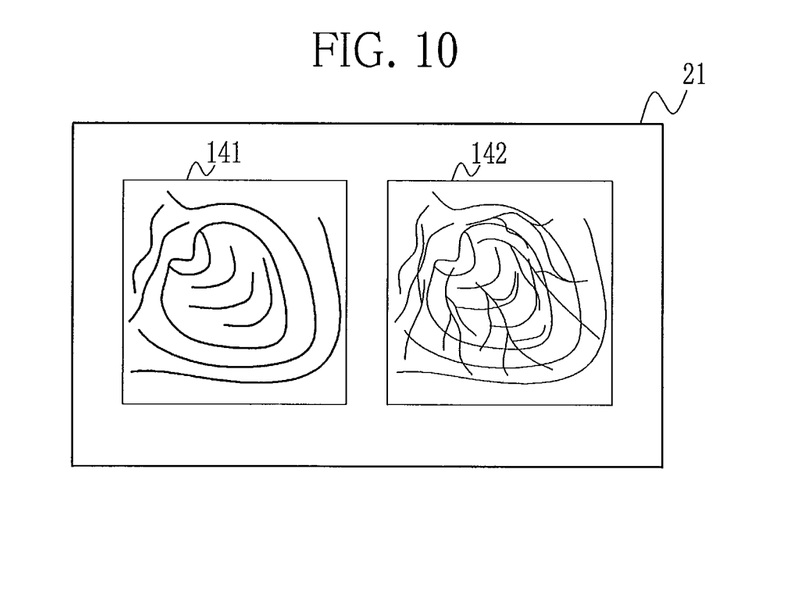
FIG. 10 is a front view of a monitor on which a normal image and a special image are displayed in a tiled manner.
Figure 11:
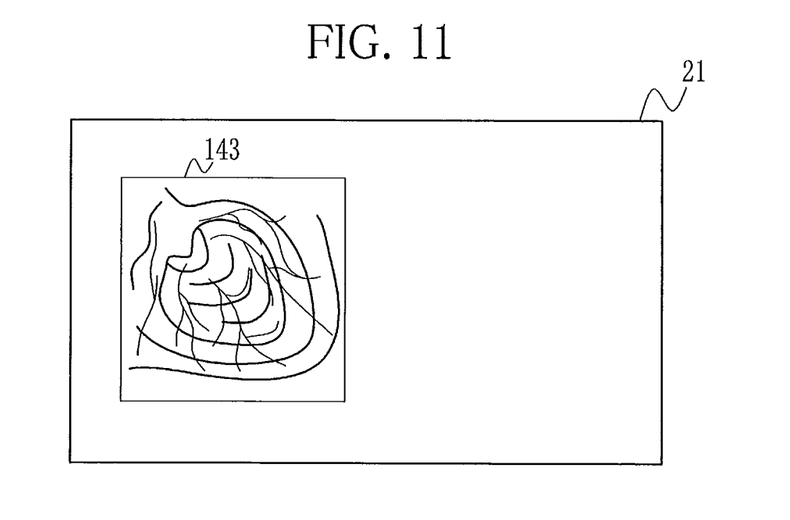
FIG. 11 is a front view of the monitor on which a composite image is displayed.

In the electronic endoscope system 10, a normal image 141 and a special image 142 may be displayed on the monitor 21 in a tiled manner as shown in FIG. 10, or a composite image 143 in which the special image 142 is superimposed on the normal image 141 may be displayed on the monitor 21 as shown in FIG. 11.

Note that, the CCD 43 and the EMCCD 46 are preferably disposed equivalently so as to have the same angle of view. The CCD 43 and the EMCCD 46 preferably have the imaging plane of the same size, the pixels (PDs 105 and 121) of the same size and number, but may have different conditions. When the CCD 43 and the EMCCD 46 have the imaging plane of different sizes and the pixels of different sizes and numbers, the DIP 64 applies image processing to the normal and special images 141 and 142 to display the normal and special images 141 and 142 on the monitor 21 in the same size. The same goes for the production of the composite image 143.

In the above embodiment, the CCD 43 is used as the image sensor for capturing the normal image, but a CMOS image sensor may be used instead of the CCD 43. However, in the CMOS image sensor, it is difficult to amplify the image signal with suppressing the noise. Thus, the CCD 43 is preferably used, as with the above embodiment. In the above embodiment, the EMCCD 46 captures the special image of the autofluorescence, but the same goes for the case of capturing agent fluorescence after administration of a fluorescent labeling agent.

In the above embodiment, both the CCD 43 and the EMCCD 46 are driven with the four phases of the vertical transfer pulses φV1 to φV4 and two phases of the horizontal transfer pulses φH1 and φH2. However, a well-known CCD driven in any of two to four phases or a virtual phase CCD may be used as the VCCD 106, 122 or the HCCD 107, 123. In the above embodiment, the EMCCD 46 captures the special image, but the EMCCD 46 may capture an image of the internal body portion irradiated with infrared right. Also, the absorptance of the infrared light may be imaged by capturing the reflected infrared light. In this case, the property of the special light cut filter 95 has to be changed in accordance with the property of the infrared light used as the special light. The same goes for the case of capturing the weak light such as the agent fluorescence reflected or emitted from the internal body portion in response to the application of the special light.

In the above embodiment, the beam splitter 42 splits the light from the internal body portion and makes the light enter into the CCD 43 and the EMCCD 46. However, a half mirror may be used instead of the beam splitter 42.

In the above embodiment, the color filter is used in not only the CCD 43 but also the EMCCD 46, but the EMCCD 46 may be a monochrome sensor without having the color filter. In the case of using the monochrome sensor as the EMCCD 46, a wavelength selection filter for selectively transmitting the autofluorescence may be provided in a front surface (imaging plane) of the EMCCD 46. In capturing the special image using the monochrome sensor as the EMCCD 46 with the wavelength selection filter, all pixels can receive the autofluorescence, and hence it is possible to obtain the special image with high resolution.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An electronic endoscope system comprising:
   an insert section to be introduced into a human body;
   a normal light emitting section for emitting white light to an internal body portion;
   a special light emitting section for emitting special light to said internal body portion;
   a first imaging section provided in a distal end portion of said insert section, for capturing a first image of said internal body portion irradiated with said white light;
   a second imaging section provided in said distal end portion of said insert section, for capturing a second image of said internal body portion irradiated with said special light, said second imaging section having an electron multiplying section for multiplying signal charge that is photoelectrically converted from weak light incident from said internal body portion;
   a control section for inputting a synchronization signal to said first imaging section and said second imaging timing section at a different timing, such that the input timing of said synchronization signal of said second imaging section is synchronized with the input timing of an electronic shutter pulse of said first imaging section, and such that the input timing of said synchronization signal of said first imaging section is synchronized with the input timing of an electronic shutter pulse of said second imaging section, and thereby setting a charge accumulation period of said first imaging section shorter than one frame period defined as an input interval of said synchronization signal and setting a charge accumulation period of said second imaging section longer than said one frame period;
   a light splitting section for splitting light incident from said internal body portion and heading said light for said first imaging section and said second imaging section; and
   a monitor for displaying said first and second images of said internal body portion.

2. The electronic endoscope system according to claim 1, wherein said second imaging section includes an excitation light cut filter for cutting out said special light reflected from said internal body portion.

3. The electronic endoscope system according to claim 1, wherein said monitor displays said first image captured by said first imaging section and said second image captured by said second imaging section in a tiled manner.

4. The electronic endoscope system according to claim 1, further comprising:
   an image composition section for producing a composite image by superimposing said second image captured by said second imaging section on said first image captured by said first imaging section, and said composite image being displayed on said monitor.

5. The electronic endoscope system according to claim 1, wherein said first imaging section and said second imaging section are disposed so as to have an equal field of view to each other with respect to said light splitting section.

6. The electronic endoscope system according to claim 1, further comprising:
   a cooling section for cooling said second imaging section.

7. The electronic endoscope system according to claim 6, wherein said cooling section includes a Peltier device.

8. The electronic endoscope system according to claim 6, wherein said cooling section includes a heat sink.

9. The electronic endoscope system according to claim 1, wherein said light splitting section includes a beam splitter.

10. The electron endoscope system according to claim 1, wherein said light splitting section includes a half mirror.

11. The electronic endoscope system according to claim 1, wherein said first imaging section includes a CCD image sensor.

12. The electronic endoscope system according to claim 1, wherein said special light is violet light having a wavelength of 400 nm to 420 nm.

13. The electronic endoscope system according to claim 1, wherein
- said second imaging section captures an infrared fluorescence image; and
- said infrared fluorescence image is displayed on said monitor together with said first image captured by said first imaging section for comparison.

* * * * *